(12) United States Patent
Bancken et al.

(10) Patent No.: US 11,435,038 B2
(45) Date of Patent: Sep. 6, 2022

(54) LIGHTING ASSEMBLY AND METHOD FOR MANUFACTURING A LIGHTING ASSEMBLY

(71) Applicant: LUMILEDS LLC, San Jose, CA (US)

(72) Inventors: Peter Henri Bancken, Eindhoven (NL); Bas Fleskens, Eindhoven (NL)

(73) Assignee: Lumileds LLC, San Jose, CA (US)

( * ) Notice: Subject to any disclaimer, the term of this patent is extended or adjusted under 35 U.S.C. 154(b) by 391 days.

(21) Appl. No.: 16/780,342

(22) Filed: Feb. 3, 2020

(65) Prior Publication Data
US 2020/0173617 A1 Jun. 4, 2020

Related U.S. Application Data

(63) Continuation of application No. 14/762,254, filed as application No. PCT/IB2014/058310 on Jan. 16, 2014, now Pat. No. 10,551,011.
(Continued)

(51) Int. Cl.
*F21K 9/90* (2016.01)
*B29C 45/14* (2006.01)
(Continued)

(52) U.S. Cl.
CPC .......... *F21K 9/90* (2013.01); *B29C 45/14639* (2013.01); *F21V 7/24* (2018.02);
(Continued)

(58) Field of Classification Search
CPC ............... H01L 33/60; B29C 45/14655; B29C 45/14639; F21V 7/24; F21V 7/28; F21Y 2115/10
See application file for complete search history.

(56) References Cited

U.S. PATENT DOCUMENTS 4,523,371 A 6/1985 Wakashima
4,593,485 A 6/1986 Thillays
(Continued)

FOREIGN PATENT DOCUMENTS

EP 0 127 239 5/1984
EP 0 921 568 9/1999
(Continued)

OTHER PUBLICATIONS

EP Article 94(3) EPC dated Mar. 29, 2016, European Application No. 14 704 666.8, 5 pages.
(Continued)

*Primary Examiner* — Marcos D. Pizarro
*Assistant Examiner* — Antonio B Crite
(74) *Attorney, Agent, or Firm* — Volpe Koenig

(57) ABSTRACT

Lighting systems are described. A lighting system includes a first lead frame portion and a second lead frame portion. The first lead frame portion has at least a top surface, a bottom surface, and an opening. The second lead frame portion is within the opening of the first lead frame portion and has at least a top surface and a bottom surface. Light-emitting diode (LED) devices are each mechanically and electrically coupled to the top surface of the first lead frame portion and the top surface of the second lead frame portion. An electrically insulating and optically reflective material is disposed over exposed regions of the top surfaces of the first and second lead frame portions.

20 Claims, 4 Drawing Sheets

Related U.S. Application Data

(60) Provisional application No. 61/756,612, filed on Jan. 25, 2013.

(51) Int. Cl.

| | | |
|---|---|---|
| *F21V 7/24* | (2018.01) | |
| *F21V 7/28* | (2018.01) | |
| *F21V 29/70* | (2015.01) | |
| *H01L 33/60* | (2010.01) | |
| *H01L 33/62* | (2010.01) | |
| *F21V 7/10* | (2006.01) | |
| *F21V 19/00* | (2006.01) | |
| *F21V 29/89* | (2015.01) | |
| *F21Y 115/10* | (2016.01) | |
| *B29L 11/00* | (2006.01) | |

(52) U.S. Cl.
CPC ............... *F21V 7/28* (2018.02); *F21V 29/70* (2015.01); *H01L 33/60* (2013.01); *H01L 33/62* (2013.01); *B29C 45/14655* (2013.01); *B29C 2045/14327* (2013.01); *B29L 2011/00* (2013.01); *F21V 7/10* (2013.01); *F21V 19/0015* (2013.01); *F21V 29/89* (2015.01); *F21Y 2115/10* (2016.08); *Y10T 29/49171* (2015.01)

(56) References Cited

U.S. PATENT DOCUMENTS

| | | |
|---|---|---|
| 5,637,914 A | 6/1997 | Tanaka et al. |
| 5,832,600 A | 11/1998 | Hashimoto |
| 6,372,859 B1 | 4/2002 | Sakata et al. |
| 7,687,815 B2 | 3/2010 | Kim |
| 7,717,591 B2 | 5/2010 | Weaver, Jr. et al. |
| 7,855,498 B2 | 12/2010 | Waffenschmidt et al. |
| 8,070,316 B2 | 12/2011 | Urano et al. |
| 8,405,096 B2 | 3/2013 | Chen et al. |
| 8,416,531 B2 | 4/2013 | Benda |
| 8,431,423 B2 | 4/2013 | Basin et al. |
| 8,445,927 B2 | 5/2013 | Joo et al. |
| 8,757,833 B2 | 6/2014 | You |
| 8,764,240 B2 | 7/2014 | Veenstra et al. |
| 8,801,232 B2 | 8/2014 | Park |
| 8,846,421 B2 | 9/2014 | Lee et al. |
| 8,899,811 B2 | 12/2014 | Jung |
| 9,379,295 B2 | 6/2016 | Kobayakawa |
| 2002/0020897 A1 | 2/2002 | Yamashita et al. |
| 2002/0084462 A1 | 7/2002 | Tamai et al. |
| 2004/0046242 A1 | 3/2004 | Asakawa |
| 2004/0075100 A1 | 4/2004 | Bogner et al. |
| 2004/0217369 A1 | 11/2004 | Nitta et al. |
| 2006/0012299 A1 | 1/2006 | Suehiro et al. |
| 2006/0231848 A1 | 10/2006 | Fu |
| 2007/0121326 A1 | 5/2007 | Nall et al. |
| 2008/0049430 A1 | 2/2008 | Sakumoto |
| 2008/0157333 A1 | 7/2008 | Lin et al. |
| 2009/0065882 A1 | 3/2009 | Shirasaka |
| 2009/0197360 A1 | 8/2009 | Han et al. |
| 2009/0296367 A1 | 12/2009 | Sekine |
| 2010/0171139 A1 | 7/2010 | Muranaka et al. |
| 2011/0049545 A1 | 3/2011 | Basin et al. |
| 2011/0057228 A1 | 3/2011 | Taniguchi et al. |
| 2011/0169031 A1 | 7/2011 | Pickard et al. |
| 2011/0169032 A1 | 7/2011 | Park |
| 2011/0193109 A1 | 8/2011 | Loh |
| 2011/0272716 A1 | 11/2011 | Lee et al. |
| 2011/0278623 A1* | 11/2011 | Kobayakawa .......... H01L 33/52 257/E33.061 |
| 2012/0015463 A1 | 1/2012 | Oyabu et al. |
| 2012/0250323 A1 | 10/2012 | Velu |
| 2012/0319150 A1 | 12/2012 | Shimomura et al. |
| 2013/0105832 A1 | 5/2013 | Peters et al. |
| 2013/0213697 A1 | 8/2013 | Palaniswamy et al. |
| 2013/0256721 A1* | 10/2013 | Chang .................. H01L 25/167 257/E33.059 |
| 2015/0008568 A1 | 1/2015 | Tsukagoshi et al. |

FOREIGN PATENT DOCUMENTS

| | | | |
|---|---|---|---|
| JP | 2007-158209 | 6/2007 | |
| JP | 2007-184237 | 7/2007 | |
| JP | 2007-184540 | 7/2007 | |
| JP | 2007184237 A * | 7/2007 | ............. F21V 19/00 |
| KR | 20090003378 | 1/2009 | |
| WO | 2012/004724 | 1/2012 | |
| WO | 2012/061182 | 5/2012 | |

OTHER PUBLICATIONS

EPO as ISA, PCT/IB2014/058310 filed Jan. 16, 2014, International Search Report and Written Opinon, dated Apr. 10, 2014.

* cited by examiner

LIGHTING ASSEMBLY AND METHOD FOR MANUFACTURING A LIGHTING ASSEMBLY

CROSS REFERENCE TO RELATED APPLICATION(S)

This application is a continuation of U.S. patent application Ser. No. 14/762,254, filed Jul. 21, 2015, which is the U.S. National Phase application under 35 U.S.C. § 371 of International Application No. PCT/IB2014/058310, filed on Jan. 16, 2014, which claims the benefit of U.S. Patent Application No. 61/756,512, filed on Jan. 25, 2013. These applications are hereby incorporated by reference herein.

FIELD OF INVENTION

The present invention generally relates to the field of lighting equipment, and specifically to a lighting assembly having a leadframe provided with an electrically insulating and optically reflective material, and to a method for manufacturing such an assembly.

BACKGROUND

Lighting assemblies comprising light emitting diode (LED) elements are of interest for various illumination applications. Mechanically stable mounting, electrical connection, and good heat dissipation are qualities of interest for achieving a high performance and long lifetime of the lighting assemblies. For illumination purposes, being able to direct the generated light is also of interest.

By mounting the LED elements on a printed circuit board (PCB) connected to a heat dissipating body, or heat sink, the LED elements are electrically connected and the heat generated during operation dissipated. One difficulty with this arrangement is however to ensure a good thermal contact between the LED elements and the heatsink. One option is to add a thermal interface material to the interface between the PCB and the heat sink.

WO 2012/004724 A1 discloses a lighting assembly wherein a LED element is fixed to a leadframe such that a mechanical mounting, electrical connection and thermal management are provided. The leadframe also comprises a light direction section that includes a reflective surface arranged to reflect light emitted from the LED element.

Although such a lighting assembly may provide a high operating performance, there is still a need for lighting assemblies with improved functionality and also methods for facilitating manufacturing of such lighting assemblies.

SUMMARY

In view of the above discussion, a concern of the present invention is to provide a method for manufacturing a lighting assembly having improved functionality.

At least one of this and other concerns of the present invention are addressed by means of a method and a lighting assembly having the features defined in the independent claims Preferable embodiments of the invention are characterized by the dependent claims.

According to a first aspect of the present invention, there is provided a method for manufacturing a lighting assembly, wherein a leadframe is provided and on which at least one light emitting diode (LED) element is arranged. The at least one LED element is configured to emit light when it is supplied with electrical power by means of the leadframe. At least a portion of the leadframe is provided with an optically reflective and electrically insulating material arranged to reflect at least a portion of the light emitted from the at least one LED element and to electrically insulate at least a portion of the leadframe.

According to a second aspect of the present invention, there is provided a lighting assembly having a leadframe with at least one light emitting diode (LED) element arranged on the leadframe, which at least one LED element is configured to emit light when supplied with electrical power by means of the leadframe. At least a portion of the leadframe is provided with an optically reflective and electrically insulating material arranged to reflect at least a portion of the light emitted from the at least one LED element, and to electrically insulate at least a portion of the leadframe.

Embodiments of the present invention are based on a realization that the functionality of the lighting assembly can be improved by providing the leadframe with a material that is both optically reflecting and electrically insulating. Using one element both for electrical connection purposes and for providing optical functions may advantageously facilitate or even enable a reduction of the number of production steps required for manufacturing of the lighting assembly, and also a reduced number of required material types, e.g. compared to a printed circuit board (PCB) based lighting assembly. Thereby a facilitated manufacturing and reduced cost may be enabled.

Embodiments of the present invention are advantageous in that they allow for a PCB to be replaced by a leadframe. Arranging the LED element directly on the leadframe provides the LED element with electrical connection and enables a good thermal contact between the LED element and the leadframe. The LED element may possibly be indirectly arranged on the leadframe, e.g. via some coupling element. The leadframe allows for the heat generated by the LED element to be dissipated from the LED elements. The leadframe may thereby act as a heat sink. By using the leadframe for providing a mechanical mounting, electrical connection and heat dissipation, the PCB and thermal interface material can be omitted which may advantageously allow for a reduced number of production steps, a reduced bill of material (BOM) required for manufacturing of the lighting assembly, and thus reduced cost.

The leadframe may for example comprise at least two not directly electrically connected portions of a sheet material comprising any material of sufficient mechanical stability and electrical conductivity. The sheet material may be cut out, etched, or stamped to form a pattern of a desired shape. The sheet material may have two parallel surface sides arranged opposite to each other, wherein at least one LED element is arranged on at least one of the surfaces. The leadframe material may advantageously be chosen such that a relatively low thermal resistance from the LED element-leadframe interface to the surroundings is achieved. The sheet material may for example comprise a metal such as copper or an alloy comprising copper and a plating applied thereon, which plating for example may be made of tin, nickel, gold, silver, or aluminum or an alloy comprising at least one of these metals. The at least two portions of the leadframe may be mechanically and/or electrically connected to each other prior to the arranging of the LED elements on the leadframe, and mechanically and/or electrically separated after the arranging of the LED elements on the leadframe. The connecting portion between the at least two portions of the leadframe may be removed for example by cutting, stamping, or etching.

In the context of the present application, the term "LED element" is used to define any device or element that is capable of emitting radiation in any region or combination of regions of the electromagnetic spectrum, for example the visible region, the infrared region, and/or the ultraviolet region, when activated e.g. by applying a potential difference across it or passing a current through it. Therefore a LED element can have monochromatic, quasi-monochromatic, polychromatic or broadband spectral emission characteristics. Each LED element has at least one light source. Examples of light sources include semiconductor, organic, or polymer/polymeric LEDs, blue LEDs, optically pumped phosphor coated LEDs, optically pumped nanocrystal LEDs or any other similar devices as would be readily understood by a person skilled in the art. RGB LEDs may advantageously be used to enable dynamic color light output from the illumination device. Furthermore, the term LED element can be used to define a combination of the specific light source that emits the radiation in combination with a housing or package within which the specific light source or light sources are placed. For example, the term LED element may refer to a bare LED die arranged in a housing, which may be referred to as a LED package. The LED element may also be domed, i.e. provided with e.g. a diffusing and/or lens shaped, light directing material.

The LED element may be arranged on the leadframe such that an electrical connection is provided between at least a first and a second portion of the leadframe and a first and a second portion of the LED element, respectively. Preferably, the LED element is mechanically fixed to the leadframe for example by soldering, electrically conductive gluing, welding, or clinching.

At least a portion of the leadframe is provided with a material, or compound, that is both electrically insulating and optically reflective. The compound may include any material that prevents electrical current from flowing between the leadframe and the surroundings, and which also is able to reflect incident light that is emitted by the LED element. Such materials include for example epoxy resin, silicones, ceramics, sol-gel glasses, polytetrafluoroethylene (PTFE), polymethyl methacrylate (PMMA), and nylon.

The compound may be provided on at least a portion of one or both of the surface sides of the leadframe, and may also be provided in between the at least first and second portions of the leadframe such that the intermediate space is partly or fully occupied by the material. The step of providing the compound may also be referred to as encapsulation, which should be interpreted as embedding at least a portion of the leadframe in the compound. The compound may be provided to the leadframe by for example molding which advantageously allows for the leadframe to be fully protected from the surroundings. By using proper leadframe design techniques, different portions of the leadframe may be electrically insulated from each other, preventing internal shortcuts, arcing, and other potential damages to the parts. Molding may also enable a smaller and more compact device, due to the possibility to encapsulate complex, three-dimensional structures, cavities, and voids with the electrically insulating and optically reflective material. Examples of molding include injection molding, transfer molding, and compression molding.

The electrically insulating and optically reflective material may also be provided by lamination, gluing, potting and/or casting.

According to an embodiment of the present invention, the at least one portion of the leadframe may be provided with the optically reflective and electrically insulating material prior to the arranging of the at least one LED element on the leadframe. This may be referred to as "pre-molding". Thereby, the at least one LED element may be protected from mechanical damage, high temperatures, etc. that may occur as the optically and electrically insulating material is provided to the leadframe. Pre-molding is also advantageous in that it may enable modularity, i.e. that similar or identical pre-molded leadframe designs could be used with different numbers and/or types of LED elements for various products or product variations.

According to another embodiment, the at least one portion of the leadframe may be encapsulated with the compound after the arranging of the at least one LED element on the leadframe. This may be referred to as "post-molding". Post-molding is advantageous in that electrical connections and leadframe edges may be encapsulated, and thus protected, by the compound. The compound may for example provide electrical insulation to the solder joints to prevent the electrically conducting parts of the lighting assembly to be touched by for example a user. The need for a protective cover of for example glass or plastic, which shields the electrically active parts of the lighting assembly from the surroundings, may thereby be reduced.

Post-molding also enables the compound, which may have a relatively high thermal conductivity as compared to e.g. air, to fill voids and cavities and thereby allow for an improved heat transfer or cooling of the lighting assembly. The mechanical reliability of the lighting assembly may also be improved as mechanically and thermally induced stresses between the LED element and the leadframe may be carried not only by the soldered joints but also by the compound.

According to an embodiment, the at least one LED element may be arranged on a first surface of the leadframe and the optically reflective and electrically insulating material provided to a second surface of the leadframe. The second surface may be arranged on a second side of the leadframe, which second side opposes a first side of the leadframe having a first surface. By encapsulating the second surface, or underside, of the leadframe, the underside may become electrically insulated or substantially electrically insulated from the surroundings. The first surface, or the upper side, may also be provided with the compound which thereby provides electrical insulation and also a reflective surface which advantageously may redirect the emitted light. A portion of the first surface may for example comprise a wall of a light-mixing chamber which may be composed mainly of optically reflecting walls within which the emitted light may be mixed to provide a uniform light output of low glare.

According to an embodiment, the at least one LED element is arranged on the leadframe by means of at least one soldered joint, thereby providing a mechanical fixation of the at least one LED element to the leadframe. The soldered joint may for example be provided by reflowing screen printed or jet printed solder paste, or by any other suitable mounting technique known in the art.

According to an embodiment, the method further comprises bending, or shaping, the leadframe to conform to any desired shape, including three-dimensional shapes. The leadframe may for example be bent such that at least a portion of the first surface of the leadframe conforms to a concave shape. Thereby an optical reflector for directing the emitted light, or a mixing chamber for mixing the light, may be achieved by means of the optically reflective and electrically insulating material. Providing a least a portion of the optical reflector or the mixing chamber with the electrically insulating and optically reflective material may advantageously improve both optical and thermal performance of the lighting assembly when operated. The leadframe may also be bent such that the first surface of the leadframe conforms to a convex shape which advantageously may facilitate dissipation of the generated heat during operation.

As the leadframe, which already is an integral part of the lighting assembly, simultaneously can be used for achieving this optical functionality and provide a heat spreader or heat sink functionality, the structure of the lighting assembly may remain relatively non-complex with a low part count, or BOM, which advantageously may enable a relatively easy and inexpensive manufacturing process.

According to an embodiment, the step of bending the leadframe is performed prior to covering the at least one portion of the leadframe with the optically reflective and electrically insulating material. This advantageously may enhance the form freedom of the lighting assembly, since the leadframe may be formed into any desired shape with a reduced risk of affecting or damaging the encapsulation.

According to an embodiment, the step of bending the sheet material is integrated with the step of covering the at least one portion of the leadframe with the optically reflective and electrically insulating material. By combining the encapsulation with the step of shaping the leadframe the manufacturing process may be simplified in terms of a reduced number of required processing steps.

According to an embodiment, the method comprises doming of the at least one LED element, wherein the LED element may be provided with e.g. a diffusing, lens shaped material.

It will be appreciated that other embodiments than those described above are also possible. It will also be appreciated that any of the features in the embodiments described above for the method for manufacturing a lighting assembly according to the first aspect of the present invention may be combined with the lighting assembly according to the second aspect of the present invention. Further objectives of, features of, and advantages with the present invention will become apparent when studying the following detailed disclosure, the drawings, and the appended claims. Those skilled in the art will realize that different features of the present invention can be combined to create embodiments other than those described in the following.

BRIEF DESCRIPTION OF THE DRAWING(S)

The above, as well as additional objects, features and advantages of the present invention, will be better understood through the following illustrative and non-limiting detailed description of preferred embodiments of the present invention, with reference to the appended drawings, in which.

Figure 3:
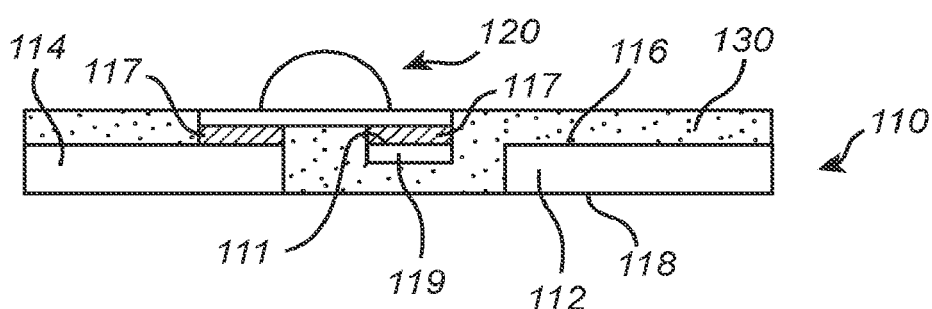
Figure 4A:
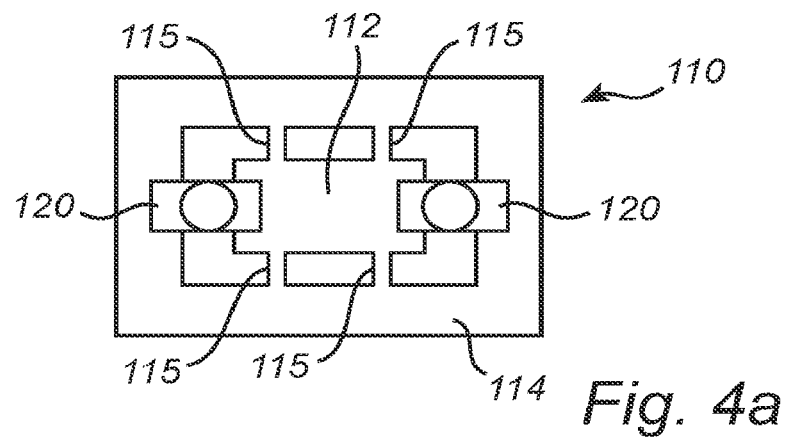
Figure 4B:
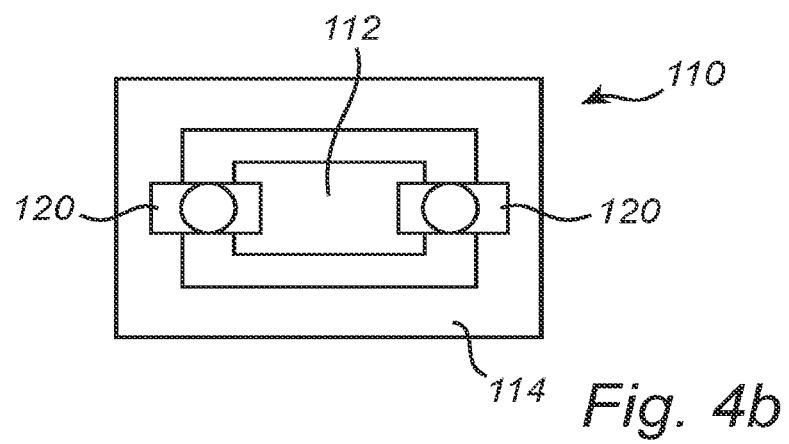
Figure 5:
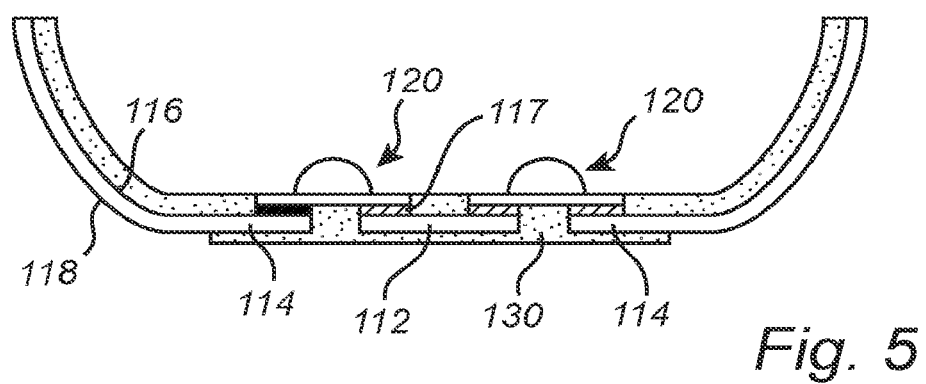
Figure 6:
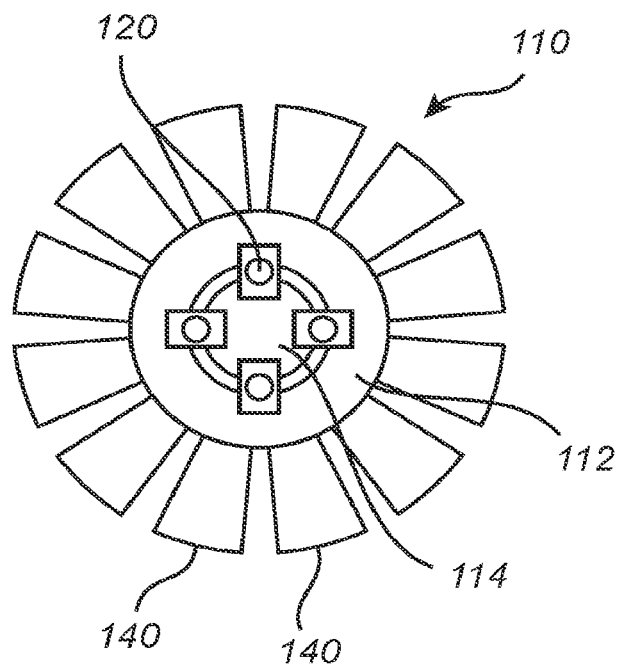
Figure 7:
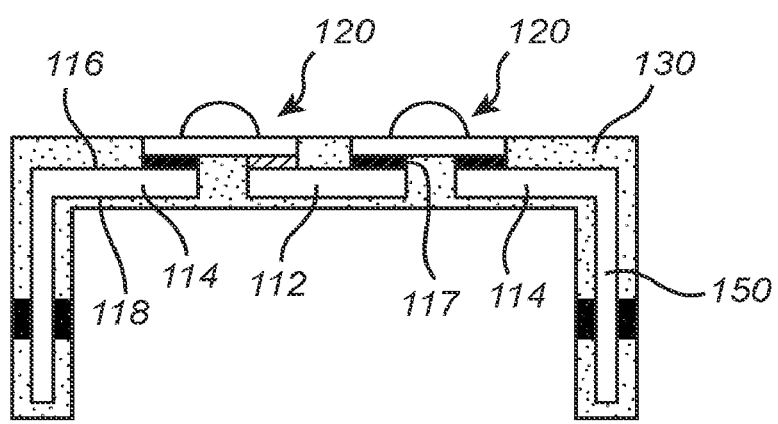

FIG. 3 schematically depicts a cross sectional side view of a lighting assembly manufactured according to an embodiment of the present invention;

FIGS. 4a and 4b schematically depict a top view of a lighting assembly according to an embodiment of the present invention, comprising a reflector formed out of a portion of the leadframe encapsulated with an electrically insulating and optically reflective material;

FIG. 5 schematically depicts a cross sectional side view of the lighting assembly of FIG. 4;

FIG. 6 schematically depicts a top view of a lighting assembly according to an embodiment of the present invention, wherein the lighting assembly comprises a heat sink formed out of a portion of the leadframe; and FIG. 7 schematically illustrates a cross sectional side view of a lighting assembly according to an embodiment of the present invention, wherein a portion of the leadframe forms a heatsink encapsulated with an electrically insulating and optically reflective material.

All the figures are schematic, not necessarily to scale, and generally only show parts which are necessary in order to elucidate the embodiments of the present invention, wherein other parts may be omitted or merely suggested.

DETAILED DESCRIPTION OF THE PREFERRED EMBODIMENT(S)

The present invention will now be described more fully hereinafter with reference to the accompanying drawings, in which exemplifying embodiments of the present invention are shown. The present invention may, however, be embodied in many different forms and should not be construed as limited to the embodiments set forth herein; rather, these embodiments are provided by way of example so that this disclosure will convey the scope of the invention to those skilled in the art. Furthermore, like numbers refer to the same or similar elements or components throughout.

Figure 1A:
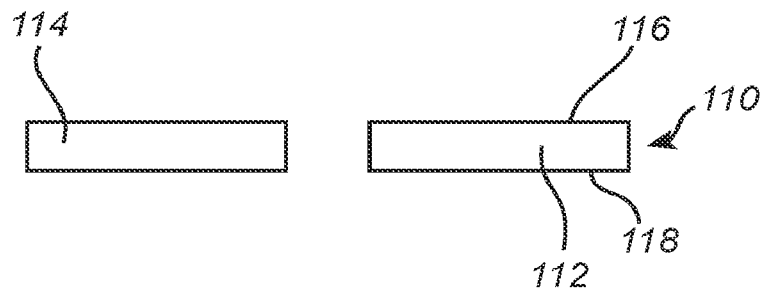
FIGS. 1a-1c illustrate a general outline of a method for manufacturing a lighting assembly according to an embodiment of the present invention.
Figure 1B:
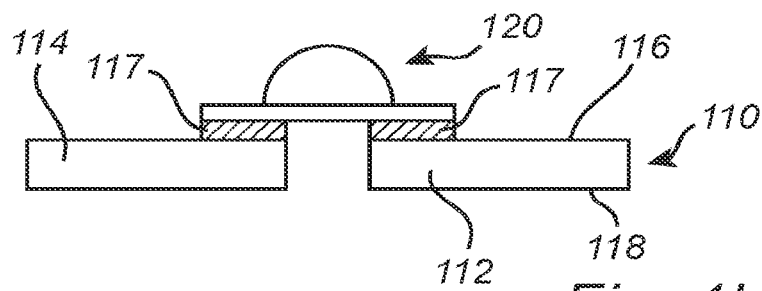
Figure 1C:
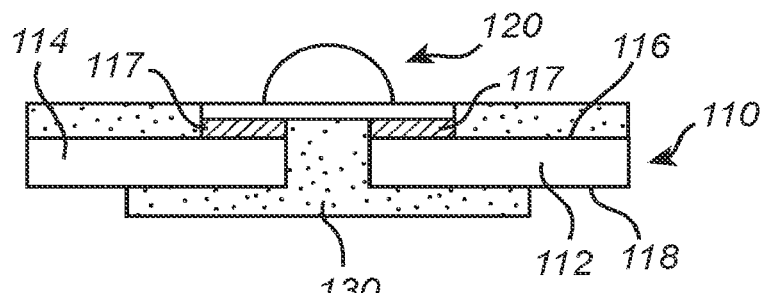

With reference to FIGS. 1a-1c, there is shown a general outline of a method for manufacturing a lighting assembly in accordance with an embodiment of the present invention.

The method comprises providing a leadframe 110, for example out of a flat metal sheet material such as a tin-coated copper sheet (FIG. 1a). The leadframe may be provided with a structure obtained for example by stamping such that leads, flanges, and not directly electrically connected first and second portions are obtained.

In the next step, a LED element 120 is arranged on the leadframe 110. The LED element 120 may for example be arranged by surface mounting, wherein solder paste is screen printed on contact pads of the first portion 112 and the second portion 114 of the leadframe 110, the LED element 120 is positioned with a pick-and-place machine, and the solder paste reflowed such that a mechanical and electrically conductive fixation is provided by solder joints 117. The resulting structure is shown in FIG. 1b.

After the mounting of the LED element 120, wherein the LED element 120 is brought in electrical contact with the leadframe, the leadframe 110 may be provided with a compound comprising an optically reflective and electrically insulating material 130. In FIG. 1c, the compound 130 is provided to the first surface 116 and a portion of the second surface 118 by foil assisted molding, in which the leadframe 110 with the LED element 120 is placed in between a bottom mold and a top mold. The top mold is provided with a soft, protective material, such as for example a foil or polyimide, which abuts the surface of the LED element 120 as the top mold is applied to the leadframe 110, and may thereby protect the LED element 120 from being provided with the compound 130 during molding. As the top mold and the foil are applied, the molding compound 130 is heated and flows into the cavity which is defined by the top and bottom molds. The compound may for example be pressed into the cavity, or sucked by means of an applied vacuum.

Figure 2A:
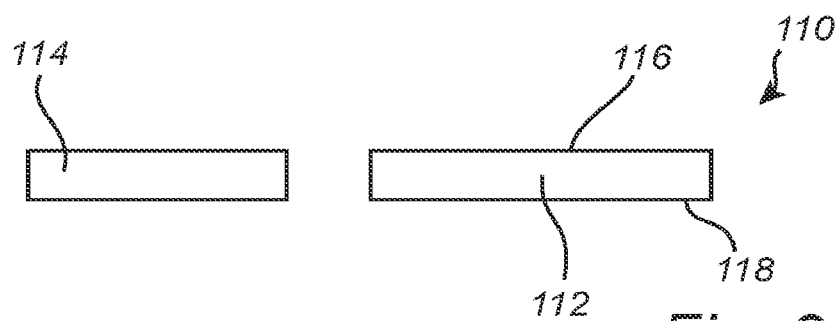
FIGS. 2a-2c illustrate an outline of a method according to another embodiment of the present invention.
Figure 2B:
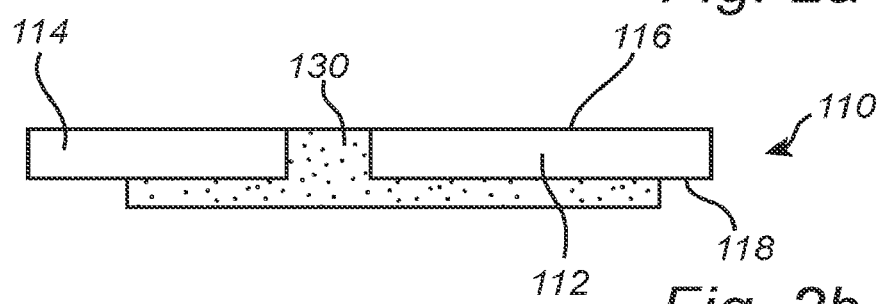
Figure 2C:
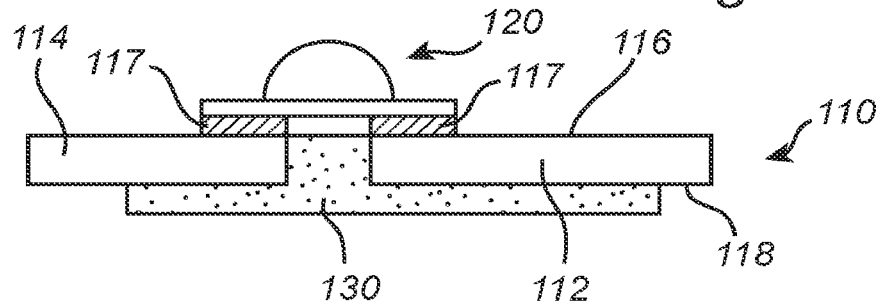

In FIGS. 2a-2c, a method for manufacturing a lighting assembly is illustrated wherein the provided leadframe 110 (FIG. 2a) is encapsulated with the compound comprising an optically reflective and electrically insulating material 130 prior to the arranging of the LED element 120 on the leadframe 110. The compound 130 may be provided to the first surface 116 of the leadframe 110, the second surface 118 of the leadframe 110, or both. The level of electrical insulation of the second surface 118 may be controlled by the surface area covered by the compound 130 and/or the thickness of the compound 130. For example, by providing the compound 130 to the electrical paths of the second side 118 of the leadframe 110, electrical insulation is provided as the remaining areas may be directly connected to a separate heatsink (not shown in the FIGS. 2a-2c), having a mating surface adapted to fit with the corresponding structure of the second surface 118 of the leadframe 110. FIG. 2b shows an example wherein the compound 130 is provided to the second surface 118 of the leadframe 110 by molding, and wherein the gap between a first and second portion 112, 114 is filled with the compound 130. After the encapsulation, the LED element 120 is mounted to the first surface 116 of the leadframe 110 as shown in FIG. 2c.

With reference to FIG. 3, the leadframe 110 may comprise a 'thinner' portion 119 which is thinner than the first portion 112 and/or the second portion 114 of the leadframe 110. The thinner portion 119 may have a first surface 111 that share a common plane with the first surface 116 of the adjacent first and second leadframe portions 112, 114, and a second surface 113 parallel with the second surface 118 of the adjacent first and second leadframe portions 112, 114. The method for manufacturing a lighting assembly may comprise a step of providing the first surface 116 of the leadframe 110 with the electrically insulating and optically reflective material 130 such that the compound 130 fills up the space between the first portion 112, the thinner portion 119, and the second portion 114 of the leadframe 110. Thereby the second surface 111 of the thinner portion 119 may be electrically insulated from the surroundings, whereas the second surface 118 of the surrounding first and second portions 112, 114 still is exposed to the surroundings. The resulting lighting assembly is shown in FIG. 3.

With reference to FIG. 4a, the first portion 112 and the second portion 114 of the leadframe may be joined by a connecting portion 115 which is comprised of the sheet material and formed at the same time as the rest of the leadframe 110 is formed, or patterned. The connecting portion 115 may hold the first portion 112 and the second portion 114 of the leadframe together such that the mechanical stability of the leadframe 110 is improved, which may facilitate the handling of the leadframe 110 e.g. during manufacturing.

Any one of the methods as described with reference to FIGS. 1a-1c, 2a-2c, and 3 may comprise a step of removing the connecting portions 115 of the leadframe 110 after encapsulation and/or mounting of the LED elements 120, for example by cutting, in order to electrically disconnect the first portion 112 and the second portion 114 of the leadframe 110 from each other. Thereby the LED elements 120 can be supplied with electrical power by means of the first and second portions 112, 114 of the leadframe 110 such that light is emitted by the LED elements 120. The resulting lighting assembly is shown in FIG. 4b. The electrical power can be supplied by an electrical power source (not shown in the figures) which may be included in the lighting assembly or connected to the lighting assembly.

The leadframe as described with reference to FIGS. 4a and 4b may constitute a unit which may be joined with a plurality of other, similar units such that a panel is formed (not shown in the figures). The units may be joined by connecting portions of the sheet material to form a panel. The units may be separated, or singulated, prior to or after encapsulation. Singulating the panel prior to encapsulation may enable easier access to each unit and provide a smooth, fully encapsulated end product. Singulating the units after the encapsulation may improve the robustness of the process flow, thereby increasing the yield.

Any one of the methods as described with reference to FIGS. 1a-1c, 2a-2c, 3, 4a and 4b may comprise a step of bending the leadframe 110 such that at least a portion of the leadframe 110 provides a heat sink dissipating the generated heat. The molding tool may be configured to form, or bend, the edge portions of the leadframe 110 during the encapsulation with the optically reflective and electrically insulating material 130, for example by pressing or applying vacuum. A separate mold may also be used, wherein the leadframe 110 is formed in a separate step prior to the encapsulation. Any portions of the leadframe 110 which are not provided with the compound 130 may also be bent into a desired shape after the molding step.

By forming the first surface 116 of the leadframe 110 such that it conforms to a concave or substantially concave shape and provide the first surface 116 with an optically reflecting layer 130, an optical reflector that redirects light emitted by the LED element 120 is provided. The resulting lighting assembly is shown in FIG. 5, wherein the optically reflecting layer 130 of the first surface 116 for example may form a wall in a mixing chamber (not shown in FIG. 5).

FIG. 6 is a top view of a lighting assembly manufactured according to the method described with reference to FIG. 5. The leadframe 110 comprises a first, inner portion 112 and a second, outer portion 114 which is provided with several flanges 140. The flanges 140 may help dissipating the heat generated by the LED elements 120. The flanges 140 are bent such that they provide an optical reflector 140 for redirecting the emitted light. The first portion 112 of the leadframe 110 is mechanically and electrically connected to the second portion 114 by means of several LED elements 120, for example according to the example depicted in FIG. 6 by four LED elements 120 that are arranged on the leadframe 110, e.g. fixated to the leadframe 110 by means of soldered joints (not shown in FIG. 6). The encapsulating compound 130 (not shown in FIG. 6), comprising an electrically insulating and optically reflective material 130, provides for mechanical support of the first and second portions 112, 114 of the leadframe 110, as well as electrical insulation from the surroundings and optical performance.

It will be appreciated that the leadframe 110, the electrically insulating and optically reflective material 130, and the LED elements 120 may be arranged in various configurations. The leadframe 110 may for example comprise three or more portions that are electrically and/or mechanically separated, which may enable individual control of the LED elements 120. The shape of the leadframe 110 may further conform to any suitable shape in order to achieve a desired optical and/or heat dissipation function.

FIG. 7 depicts an example of a lighting assembly manufactured in accordance with a method according to an embodiment of the present invention. The lighting assembly comprises a leadframe 110 having a first portion 112 and a second portion 114 provided with flanges 150, forming (part of) a heat sink 150. The flanges 150 are provided by bending the second portion of the leadframe downwards, i.e. in a direction away from the first surface of the leadframe onto which the LED elements 120 are arranged by means of soldered joints 117. The encapsulation compound 130 is provided on the first surface 116 and second surface 118 of the leadframe 110, which may enable incident light to be reflected.

In conclusion, a method for manufacturing a lighting assembly is disclosed, wherein a LED element is arranged on a leadframe. The LED element is configured to emit light when supplied with electrical power by means of the leadframe. At least a portion of the leadframe is provided with an optically reflective and electrically insulating material arranged to reflect light emitted from the LED element and to electrically insulate at least a portion of the leadframe. A lighting assembly comprising the LED element and the leadframe is also disclosed.

While the present invention has been illustrated and described in detail in the appended drawings and the foregoing description, such illustration and description are to be considered illustrative or exemplifying and not restrictive; the present invention is not limited to the disclosed embodiments. Other variations to the disclosed embodiments can be understood and effected by those skilled in the art in practicing the claimed invention, from a study of the drawings, the disclosure, and the appended claims. The mere fact that certain measures are recited in mutually different dependent claims does not indicate that a combination of these measures cannot be used to advantage. Any reference signs in the claims should not be construed as limiting the scope.

What is claimed is:

1. A lighting system comprising:
   a first lead frame portion comprising at least a top surface, a bottom surface, and an opening; and
   a second lead frame portion within the opening of the first lead frame portion and comprising at least a top surface and a bottom surface;
   a plurality of light-emitting diode (LED) devices each mechanically and electrically coupled to the top surface of the first lead frame portion and the top surface of the second lead frame portion; and
   an electrically insulating and optically reflective material over exposed regions of the top surfaces of the first and second lead frame portions.

2. The lighting system of claim 1, wherein the electrically insulating and optically reflective material is further under at least a portion of at least one of the bottom surface of the first lead frame portion and the bottom surface of the second lead frame portion.

3. The lighting system of claim 2, wherein the first lead frame portion and the second lead frame portion are separated by a space, and the electrically insulating and optically reflective material fills the space.

4. The lighting system of claim 1, wherein the second lead frame portion comprises a thick portion and a thin portion spaced apart from the thin portion.

5. The lighting system of claim 4, wherein each of the plurality of LEDs is mechanically coupled to the thin portion of the second lead frame portion.

6. The lighting system of claim 4, wherein the electrically insulating and optically reflective material further fills gaps between the thick portion and the thin portion of the second lead frame portion and between the second lead frame portion and the first lead frame portion.

7. The lighting system of claim 1, wherein at least a portion of the first lead frame portion has a shape that curves toward the plurality of LEDs.

8. The lighting system of claim 7, wherein the shape is a concave shape with the top surfaces of the first and second lead frame portions inside the concave shape.

9. The lighting system of claim 7, wherein a plurality of notches extend into outer edges of the first lead frame portion to form a plurality of spaced apart flanges.

10. The lighting system of claim 1, wherein at least a portion of the first lead frame portion has a shape that includes a flat portion and a portion that bends away from the plurality of LEDs.

11. The lighting system of claim 10, wherein the portion that bends away from the plurality of LEDs is covered by the electrically insulating and optically reflective material on both the top and bottom surfaces.

12. The lighting system of claim 10, wherein the the portion that bends away from the plurality of LEDs is bent at a 90° angle with respect to flat portion of the first lead frame portion.

13. The lighting system of claim 10, wherein notches are formed in outer edges of the portion that bends away from the plurality of LEDs to form a plurality of spaced apart flanges.

14. The lighting system of claim 1, wherein each of the plurality of LEDs comprises at least a first electrode electrically and mechanically coupled to the first lead frame portion and a second electronic electrically and mechanically coupled to the second lead frame portion.

15. The lighting system of claim 1, wherein the first lead frame portion and the second lead frame portion comprise tin-coated copper.

16. A lighting system comprising:
    a first lead frame portion comprising:
       a flat region with an opening therethrough, and
       a plurality of spaced apart flanges mechanically coupled to outer edges of the flat region and having a concave shape relative to the flat portion;
    a second lead frame portion within the opening through the flat region of the first lead frame portion;
    a plurality of light-emitting diodes (LEDs) mechanically and electrically coupled within the concave shape to the second lead frame portion and the flat region of the first lead frame portion; and
    an electrically insulating and optically reflective material covering at least exposed regions of a surface of the first lead frame portion and the second lead frame portion inside the concave shape.

17. The lighting system of claim 16, wherein the electrically insulating and optically reflective material further covers at least regions of a surface of the first lead frame portion and the second lead frame portion opposite the plurality of LEDs.

18. A lighting system comprising:
    a first lead frame portion comprising:
       a flat region with an opening therethrough, the flat region comprising at least a top surface and a bottom surface, and
       a bent region bent away from the top surface of the flat region at an angle;
    a second lead frame portion within the opening through the flat region of the first lead frame portion, the second lead frame portion comprising at least a top surface and a bottom surface;
    a plurality of light-emitting diodes (LEDs) mechanically and electrically coupled to the top surface of the flat region of the first lead frame portion and the top surface of the second lead frame portion; and
    an electrically insulating and optically reflective material over at least exposed regions of the top surfaces of the first and second lead frame portions.

19. The lighting system according to claim 18, wherein the electrically insulating and optically reflective material covers at least regions of the bottom surfaces of the first and second lead frame portions.

20. The lighting system according to claim 18, wherein the angle is 90°.

* * * * *